（12）United States Patent
Gibson

(10) Patent No.: US 7,250,562 B2
(45) Date of Patent: Jul. 31, 2007

(54) LETTUCE VARIETY DESIGNATED "STURGIS"

(75) Inventor: George D. Gibson, Salinas, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 11/285,934

(22) Filed: Nov. 23, 2005

(65) Prior Publication Data

US 2006/0112455 A1 May 25, 2006

Related U.S. Application Data

(60) Provisional application No. 60/630,807, filed on Nov. 24, 2004.

(51) Int. Cl.
*A01H 5/00* (2006.01)
*A01H 5/10* (2006.01)
*A01H 1/00* (2006.01)

(52) U.S. Cl. ............... 800/305; 800/260; 435/410

(58) Field of Classification Search .............. 800/260, 800/305; 435/410
See application file for complete search history.

(56) References Cited

OTHER PUBLICATIONS

Poehlman, J.M. and D.A. Sleper. 1995. Breeding Field Crops. 4th ed. Iowa State University Press, Ames, Iowa, p. 473.*

\* cited by examiner

*Primary Examiner*—David H. Kruse
*Assistant Examiner*—Keith O. Robinson
(74) *Attorney, Agent, or Firm*—Morrison & Foerster LLP

(57) ABSTRACT

A new lettuce variety designated *Sturgis* is described. *Sturgis* is a romaine lettuce variety exhibiting stability and uniformity.

14 Claims, 1 Drawing Sheet

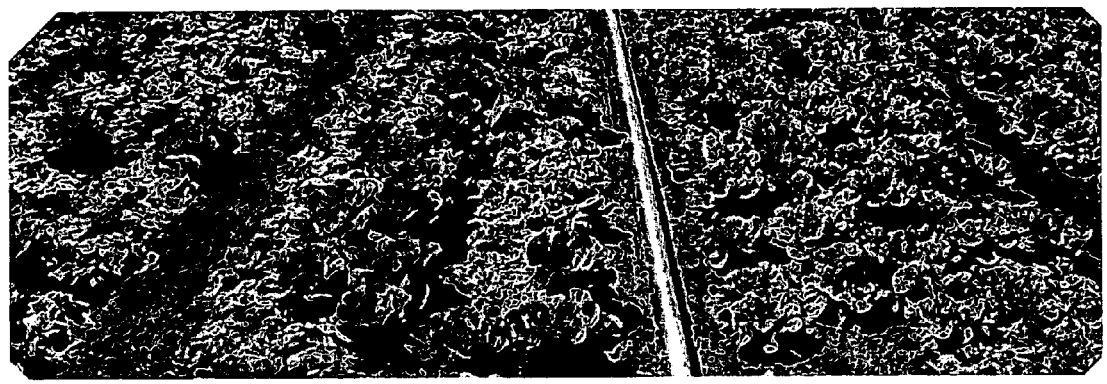

LETTUCE VARIETY DESIGNATED "STURGIS"

I. RELATED APPLICATION

This application claims benefit under 35 USC § 119(e) to U.S. Provisional application No. 60/630,807, filed Nov. 24, 2004 which is hereby incorporated by reference in its entirety.

II. FIELD OF THE INVENTION

This invention relates to the field of plant breeding. In particular, this invention relates to a lettuce, *Lactuca sativa*, variety, *Sturgis*.

III. BACKGROUND OF THE INVENTION

Lettuce is an increasingly popular crop. Worldwide lettuce consumption continues to increase. As a result of this demand, there is a continued need for new lettuce varieties. In particular, there is a need for improved romaine lettuce varieties that exhibit improved growth habits, bolting, tolerance, tip burn tolerance and disease resistance.

IV. SUMMARY OF THE INVENTION

In order to meet these needs, the present invention is directed to an improved romaine lettuce variety with a dark green color and open growth habit that forms a very dense and open heart and higher tolerance to bolting and tip burn as well as improved virus resistance. In particular, the present invention is directed to lettuce, *Lactuca sativa*, seed designated as *Sturgis* having ATCC Accession Number PTA-7228. This variety is also know as PRO 1432. The present invention is further directed to a lettuce, *Lactuca sativa* plant and parts isolated therefrom produced by growing *Sturgis* lettuce seed. The present invention is further directed to a *Lactuca sativa* plant and parts isolated therefrom having all the physiological and morphological characteristics of a *Lactuca sativa* plant produced by growing *Sturgis* lettuce seed having ATCC Accession Number PTA-7228. The present invention is further directed to an $F_1$ hybrid lettuce, *Lactuca sativa* seed, plants grown from the seed and a head isolated therefrom having *Sturgis* as a parent wherein *Sturgis* is grown from *Sturgis* lettuce seed having ATCC Accession Number PTA-7228.

Lettuce plant parts include lettuce heads, lettuce leaves, parts of lettuce leaves, pollen, ovules, flowers and the like. The present invention is further directed to lettuce heads, lettuce leaves, parts of lettuce leaves, flowers, pollen and ovules isolated from *Sturgis* lettuce plants. The present invention is further directed to tissue culture of *Sturgis* lettuce plants.

The present invention is further directed to packaging material containing *Sturgis* plant parts. Such packaging material includes but is not limited to boxes, plastic bags, etc. The *Sturgis* plant parts may be combined with lettuce plant parts of other plant varieties.

The present invention is further directed to a method of selecting lettuce plants comprising a) growing *Sturgis* lettuce plants wherein the *Sturgis* plants are grown from lettuce seed having ATCC Accession Number PTA-7228 and b) selecting a plant from step a). The present invention is further directed to lettuce plants, plant parts and seeds produced by the lettuce plants wherein the lettuce plants are isolated by the selection method of the invention.

The present invention is further directed to a method of breeding lettuce plants comprising crossing a lettuce plant with a plant grown from *Sturgis* lettuce seed having ATCC Accession Number PTA-7228. The present invention is further directed to lettuce plants, lettuce parts from the lettuce plants and seeds produced therefrom where the lettuce plant is isolated by the breeding method of the invention.

V. BRIEF DESCRIPTION OF THE DRAWINGS

The invention will be better understood by reference to the following Figure.

FIG. 1 shows a comparison of the appearance of *Sturgis* and Frontier Cos in a field infected with Tomato Bushy Stunt Virus. Symptoms of viral infection are seen in the Frontier Cos plants (left), but not in the resistant *Sturgis* plants on the right. Symptoms are demonstrated as flattened plants exhibiting no delectable leaf turgor.

VI. DETAILED DESCRIPTION OF THE INVENTION

In order to more clearly understand the invention, the following definitions are provided:

Romaine Lettuce: Romaine lettuce is *Lactuca sativa* L. var. *longifolia* Lam; also known as Cos. The plant develops in an upright open or upright compact growing habit with coarse textured leaves. The leaves are longer than they are wide, cupping together to form an elongated loose head. Leaf margins are often entire or undulated, rarely frilled. Other leaves range in color from light green to dark green with a heavy midrib. Inner heart leaves are smaller and range from light yellow to light green in color.

Core Length: Core length is the length of the internal lettuce stem. Core length is measured from the base of the cut head to the tip of the core.

Core Diameter: Core diameter is the diameter of the lettuce stem at the base of the cut head.

Romaine Heart: Romaine heart is the densest part of the romaine plant often yellow and light green in color and of succulent texture. The heart is generally enclosed by two to three outer darker green leaves.

Heart Length: Heart length is the length of the vertically sliced lettuce plant as measured from the base of the cut stem to the top leaf margin of the longest outermost leaf that encloses the romaine heart.

Head Length: Core Length Ratio: The ratio of the head length to core length is indicative of the percentage of useable product produced by the lettuce plant.

Plant Diameter: The plant diameter is a measurement across the top of the lettuce plant at its widest point. The measurement of frame diameter is taken from the outer most leaf tip horizontally to the outer most leaf tip.

Head Weight: Head weight is the weight of the marketable lettuce plant, cut and trimmed to market specifications.

Rogueing: Rogueing is the process in lettuce seed production where undesired plants are removed from a planting of a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a romaine lettuce variety, a romaine plant is at a marketable state when the heart has some density and the head has reached an adequate size and weight.

PIC Type: PIC is an acronym for Paris Island Cos, a specific type and characterization of romaine lettuce. A PIC type romaine refers to an often vigorous growing romaine type with a smooth leaf surface. PIC type romaine varieties are often less heat resistant and faster growing than Florida type romaines.

Florida Type: A Florida type romaine refers to a specific class of romaine varieties with improved heat and bolting resistance, a more savoyed leaf surface, and corky root resistance. This class of romaine is often less vigorous and slower growing than the PIC type.

Tomato Bushy Stunt: Tomato Busy Stunt is a viral disease caused by infection with a Tombusvirus known to infect lettuce. Resistance to Tomato Busy Stunt refers to a level of resistance in a lettuce variety as measured by visual symptoms. Resistance is deemed present when symptoms are not present in at least 85% of a lettuce variety when exposed to Tomato Bushy Stunt virus. For example, see FIG. 1 which shows the resistance of *Sturgis* plants to Tomato Bushy Shunt Virus compared to Frontier Cos plants.

Taking into account these definitions, the present invention is directed to seeds of the lettuce variety *Sturgis*, plants produced by growing *Sturgis* lettuce seeds, plant parts from the plants, one or more plants selected from a collection of *Sturgis* plants, seeds derived or produced therefrom and plant parts isolated therefrom; plants produced by crossing a lettuce plant with a *Sturgis* lettuce plant and seeds derived or produced therefrom.

VII. Origin and Breeding History of the Variety *Sturgis*

*Sturgis* is a romaine lettuce variety developed from a hand pollinated cross of the commercial varieties Prara Cos and Frontier Cos, both available from Central Valley Seeds. The initial cross was made in San Joaquin Valley of California in the vicinity of the town of Corcoran, Calif. in a development seed production field. The F1 seed harvested was designated as # 9992X9940. Prara Cos, a dark green PIC type was selected as a source of dark color, weight, and heart density. Frontier Cos, was selected as it is characteristically slow maturing and is an excellent source for the desired slow bolting characteristics and tip burn resistance. The cross was made to produce a dark green, slow maturing, slow bolting romaine variety, with a dense heart and a strong tolerance to tip burn. *Sturgis* is adapted to the Salinas Valley, Calif. and the Yuma, Ariz. growing regions.

The following year, approximately 50 plants of the F1 seed were planted in a San Joaquin Valley research seed production field for seed increase. The F2 seed was harvested in bulk and labeled SJ00MV116.

More than 300 F2 populations including the SJ00MV116 line were planted in a research and development field trial in Salinas Valley, Calif. the following year. Individual F2 plants were selected at market maturity for particular distinguishing characteristics in type, size, color, days to bolting and resistance to tip burn. The particular selection labeled RSV01006-182-1 was noted to be extremely dark in color compared to the parent variety Frontier Cos, have an increased heart density compared to the parent variety Frontier Cos, was slower bolting compared to the parent variety Prara Cos, and did not show any signs of tip burn. More than 600 plants were selected and removed from the trial, and allowed to fully mature in the inventors' green house facility. The F3 seed from the selections was harvested in the early fall the following year.

A single F3 seed from each selection was replanted in a green house facility immediately following the final F3 seed harvest. Selection number RSV01006-182-1 was included, and the F4 seed from the single plant was harvested in the early spring of the following year. The F4 seed was labeled SMG1RSV01006-1-82-1.

The F4 seed from the single plant was then increased in a research and development seed production crop in the San Joaquin Valley during that year, near the town of San Joaquin, Calif. The line, PSJV02848 was noted as segregating for type, maturity and color. 15 individual plants were selected at market maturity; the selected plants best demonstrated a darker color, slower maturity and dense hearts as compared to other plants in the population and the parent varieties. The remaining block was selectively rogued, and the F5 bulk seed and the F5 individual plants were harvested in the fall of that planting season.

The F5 bulk line, PSJV02848 was included in a trial in the early spring of the following year, arranged through the USDA as part of a screen for romaine varieties for resistance to Tomato Bushy Stunt Virus. A total of 80 lines were included to be screened. Of the 80 lines, only PSJV02848 proved to be resistant to Tomato Bushy Stunt Virus. All other plants tested were either severely stunted or completely killed by the virus. At the time of maturity, it was noted that F5 line PSJV02848 was segregating for type and maturity, but completely resistant to the Bushy Stunt Virus disease, as no plants were affected by the virus.

Upon this observation, 15 F5 individual plant selections of line PSJV02848 were sourced. These 15 lines were then included in a late planting into a research and development seed production crop in San Joaquin Valley, Calif. during the following year. These 15 selections, the bulk seed line, and susceptible check varieties were also simultaneously trialed on three separate locations in the Salinas Valley known to be infected with the Tomato Bushy Stunt Virus during the following summer. The 15 F5 sister lines were evaluated in all 3 trials and item PSJV02848-14 consistently rated highest in all 3 trials. In all evaluations, this item demonstrated the desired dark color, increased heart weight, slow maturity, slow bolting and resistance to tipburn and resistance to tomato bushy stunt virus. This item was selectively rogued for type, color and maturity in the research seed production block, and the F6 seed was harvested in bulk in August of that year. An additional 8 F6 individual plants were also harvested separately. The F6 bulk seed was produced as stake number PSJV032105, and noted as uniform and stable in the seed production block. In September of that year, the F6 bulk seed line was designated PX 432, now known as *Sturgis*.

A portion of PX 432 was then again increased in the Southern hemisphere (Australia), planted in October of that year. The block was selectively rogued for type and maturity and the bulk F7 seed was harvested in bulk in the early spring of the following year. The F7 generation of PX 432 was noted as uniform and stable and without variants as evaluated in the seed production field.

The F7 seed of PX 432 was immediately processed and a portion of the F7 seed was used as stock seed to increase the variety. The F7 seed was planted in a San Joaquin Valley, Calif. summer seed production field in Spring. The F7 plants were selectively rogued for type and maturity, and the F8 seed was harvested in bulk in the fall. Field trials of the F7 seed were conducted during the summer. *Sturgis* continued to demonstrate the dark green color, improved heart weight, slow maturity, slow bolting, and resistance to tip burn and Tomato Bushy Stunt Virus.

*Sturgis* has been as observed in multiple field trials and in seed production crops to be uniform, stable, and without variants for 2 generations.

*Lactuca sativa* cultivar *Sturgis* has numerous distinguishing characteristics as outlined in the following list:

*Sturgis* Description Information

| | |
|---|---|
| Plant Type: | PIC |
| Seed: | |
| Seed Color: | Black |
| Light Dormancy: | None |
| Heat Dormancy: | None |
| Cotyledons: | |
| Shape of Cotyledons: | Spatulate |
| Shape of Fourth Leaf: | Spatulate |
| Length/Width Index of Fourth Leaf: | |
| Apical Margin: | Entire |
| Basal Margin: | Entire |
| Undulation: | None |
| Green Color: | Dark |
| Anthocyanin: | None |
| Distribution: | |
| Rolling: | None |
| Cupping: | None |
| Reflexing: | None |
| Mature Leaves: | |
| Margin: | Entire |
| Incision Depth (Deepest penetration of the margin): | None |
| Indentation (Finest Division of the Margin): | None |
| Undulation of the Apical Margin: | Slight |
| Green Color: | Dark |
| Anthocyanin | None |
| Distribution: | None |
| Size: | Intermediate |
| Glossiness: | Glossy |
| Blistering: | Slight |
| Leaf Thickness: | Thick |
| Trichomes: | Absent |

Comparison of *Sturgis* to the Parent Lines

| Characteristic | Sturgis | Prara Cos | Frontier cos |
|---|---|---|---|
| Bolting Class | Slow | Intermediate | Slow |
| Color | Dark | Dark | Light |

Growing Season

| Season | Sturgis | Prara Cos | Frontier cos |
|---|---|---|---|
| Spring area | Salinas Valley, CA | Salinas Valley, CA | Salinas Valley, CA |
| Summer area | Salinas Valley, CA | Salinas Valley, CA | Salinas Valley, CA |
| Fall area | Salinas Valley, CA | Salinas Valley, CA | Salinas Valley, CA |

Diseases and Stress Reactions

| Disease or Stress | Sturgis | Prara Cos | Frontier cos |
|---|---|---|---|
| Tomato Bushy Stunt | Resistant | Susceptible | Susceptible |
| Big Vein: | Susceptible | Susceptible | Susceptible |
| Lettuce Mosaic: | Susceptible | Susceptible | Susceptible |
| Cucumber Mosaic: | Susceptible | Susceptible | Susceptible |

Physiological/Stress

| Stress | Sturgis | Prara Cos | Frontier cos |
|---|---|---|---|
| Tipburn | Tolerant | Susceptible | Tolerant |
| Heat | Tolerant | Susceptible | Tolerant |

Breeding and Selection

The present invention is further directed to the use of *Sturgis* lettuce in breeding and selection of new varieties.

A. Breeding

In lettuce breeding, lines are selected for certain desired appropriate characteristics. For example, one line may be selected for bolt tolerance in the fall growing conditions of the desert production locations of California and Arizona or for resistance to viruses such as Tomato Bushy Stunt. Another line may be selected for the size, color and texture of the lettuce head. Crosses are made by hand, for example, to produce a dark green, tip burn resistant romaine lettuce with improved texture, and size for fall plantings in Yuma Ariz., and Huron Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possibilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art. In the present invention, Para Cos and Frontier Cos were crossed.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

Deposit Information Applicants have made available to the public without restriction a deposit of at least 2500 seeds of lettuce variety *Sturgis* with the American Type Culture Collection (ATCC), P.O. Box 1549, MANASSAS, Va. 20108 USA, with a deposit on Nov. 28, 2005 which has been assigned ATCC number PTA-7228.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

VIII. EXAMPLES

Example 1

General Trialing Method

I. Set Up

The following steps illustrate the general trialing method of the invention.
1. A trial is set up to compare one or more lines. Parental lines and related varieties are identified.
2. Primary slots are identified.
3. Accession lines are located and purchased/obtained from seed dealers or growers.
4. All varieties are assigned a number to maintain integrity and anonymity.
5. Trials are set up in with all necessary varieties. Variety arrangement for trial is diagramed.

II. Planting
1. Commercial plantings are located by contacting commercial growers during the planting slot recommended for the variety.
2. A field is located during commercial planting and the necessary rows and area is marked off.

3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance
1. All tested varieties are treated identically. Plants are watered, fertilized, and treated to control pests in the same manner as other lettuce plants in the commercial field.
2. The trial is thinned to separate the plants for optimum growth.

IV. Evaluation
1. Evaluations are done as near to the time of the commercial harvest as possible.
2. The evaluation is conducted "blindly". The evaluator(s) do not have the key to the trial at the time of evaluation.
3. 24 heads of each variety are evaluated.
  a. The frame diameter of 24 random plants are measured to the nearest cm.
  b. 24 mature heads of each variety are cut to the cap leaf.
  c. The heads are carried to an adequate work station
  d. The following measurements are then conducted and recorded:
   1. Each head is weighed to the nearest gram.
   2. The core diameter of each head is measured to the nearest mm.
   3. The heads are then sliced in to halves, discarding 1 half.
   4. The core lengths (from the cut stem to the core tip) are measured to the nearest mm.
   5. The plant length (from the cut stem to the cap leaf) is measured to the nearest mm.
   6. The plant diameter (at its widest point) is measured to the nearest mm.
   7. The heart length is measured to the nearest mm.
   8. The ideal maturity or harvest date is then estimated based on the solidity of the head, the core length and any other physiological characteristics present.
   9. The leaf color is documented using the Munsell Color Charts for Plant Tissue.
  e. From these measurements, an Excel program is used to calculate the averages, the standard deviations and the T-Tests for the compared varieties.

Example 2

Comparative Analysis

Following the procedures of Example 1, *Sturgis* romaine lettuce was compared to various other varieties. Comparative data was obtained and analyzed for different romaine lettuce lines. Core length, core diameter, head diameter, head length, average head diameter, frame diameter and head weight as provided in the definitions section above were determined.

*Sturgis* is a distinct romaine lettuce variety with a dark green color and open growth habit compared to similar varieties. This variety is slow growing and forms a very dense and heavy open heart. Where as the heart of most varieties are formed as the outer leaves cup in to enclose the denser part of the internal romaine plant, the heart of *Sturgis* remains open and uncupped. Though the heart is not cupped in by the outer leaves, the heart is formed by a very dense conglomeration of internal leaves increasing the weight and the yield of the plant. This variety also demonstrates a high tolerance to bolting and tip burn which allows it to be grown in regions of California and Arizona where many romaine varieties cannot be planted.

Comparative testing results are presented in Tables 1A-C, 2A-C, 3A-C and 4A-C.

TABLE 1A

|  | Days to Maturity |
|---|---|
| Sturgis | 79 |
| Prara Cos | 78 |
| Frontier | 81 |

TABLE 1B

|  | Core Length (mm) | | Head wt. (g) | |
|---|---|---|---|---|
| Sample # | Sturgis | Prara Cos | Sturgis | Prara Cos |
| 1 | 24 | 30 | 750 | 687 |
| 2 | 27 | 30 | 885 | 669 |
| 3 | 28 | 32 | 890 | 545 |
| 4 | 24 | 24 | 854 | 609 |
| 5 | 24 | 30 | 860 | 678 |
| 6 | 25 | 32 | 725 | 702 |
| 7 | 29 | 35 | 700 | 754 |
| 8 | 20 | 35 | 890 | 698 |
| 9 | 20 | 35 | 700 | 785 |
| 10 | 24 | 34 | 785 | 668 |
| 11 | 28 | 37 | 745 | 734 |
| 12 | 29 | 35 | 715 | 600 |
| Average | 25.2 | 32.4 | 791.6 | 677.4 |
| Stan dev | 3.13E+00 | 3.55E+00 | 7.84E+01 | 6.75E+01 |
| T test | 2.53E−05 | | 9.32E−04 | |
| Probability % | 100.0 | | 99.9 | |
| % Difference | 77.6 | | 85.6 | |

TABLE 1C

|  | Core Length (mm) | | Plant Height (cm) | |
|---|---|---|---|---|
| Sample # | Sturgis | Frontier | Sturgis | Frontier |
| 1 | 24 | 55 | 27 | 31 |
| 2 | 27 | 40 | 29 | 31 |
| 3 | 28 | 45 | 29 | 30 |
| 4 | 24 | 60 | 27 | 31 |
| 5 | 24 | 65 | 28 | 30 |
| 6 | 25 | 62 | 30 | 30 |
| 7 | 29 | 50 | 30 | 31 |
| 8 | 20 | 55 | 29 | 33 |
| 9 | 20 | 43 | 28 | 31 |
| 10 | 24 | 39 | 27 | 30 |
| 11 | 28 | 40 | 30 | 30 |
| 12 | 29 | 40 | 27 | 31 |
| Average | 25.2 | 49.5 | 28.4 | 30.8 |
| Stan dev | 3.13E+00 | 9.59E+00 | 1.24E+00 | 8.66E−01 |
| T test | 2.83E−08 | | 2.30E−05 | |
| Probability % | 100.0 | | 100.0 | |
| % Difference | 50.8 | | 92.4 | |

TABLE 2A

|  | Days to Maturity |
|---|---|
| Sturgis | 66 |
| Prara | 65 |
| Frontier | 68 |

TABLE 2B

|  | Core Length (mm) | | Head wt. (g) | |
|---|---|---|---|---|
| Sample # | Sturgis | Prara Cos | Sturgis | Prara Cos |
| 1 | 27 | 39 | 698 | 675 |
| 2 | 24 | 37 | 711 | 690 |
| 3 | 27 | 40 | 745 | 745 |
| 4 | 28 | 40 | 789 | 603 |
| 5 | 30 | 37 | 823 | 756 |
| 6 | 25 | 40 | 683 | 645 |
| 7 | 29 | 35 | 703 | 678 |
| 8 | 32 | 35 | 785 | 654 |
| 9 | 32 | 39 | 698 | 702 |
| 10 | 34 | 30 | 732 | 673 |
| 11 | 30 | 34 | 667 | 700 |
| 12 | 28 | 37 | 799 | 692 |
| Average | 28.8 | 36.9 | 736.1 | 684.4 |
| Stan dev | 2.95E+00 | 3.03E+00 | 5.14E+01 | 4.13E+01 |
| T test | 1.16E−06 | | 1.27E−02 | |
| Probability % | 100.0 | | 98.7 | |
| % Difference | 78.1 | | 93.0 | |

TABLE 2C

|  | Core Length (mm) | | Plant Height (cm) | |
|---|---|---|---|---|
| Sample # | Sturgis | Frontier | Sturgis | Frontier |
| 1 | 27 | 35 | 28 | 30 |
| 2 | 24 | 40 | 27 | 30 |
| 3 | 27 | 40 | 29 | 28 |
| 4 | 28 | 45 | 29 | 29 |
| 5 | 30 | 79 | 25 | 30 |
| 6 | 25 | 78 | 27 | 31 |
| 7 | 29 | 50 | 26 | 31 |
| 8 | 32 | 65 | 28 | 30 |
| 9 | 32 | 78 | 29 | 29 |
| 10 | 34 | 45 | 25 | 31 |
| 11 | 30 | 67 | 26 | 32 |
| 12 | 28 | 70 | 28 | 30 |
| Average | 28.8 | 57.7 | 27.3 | 30.1 |
| Stan dev | 2.95E+00 | 1.68E+01 | 1.48E+00 | 1.08E+00 |
| T test | 6.65E−06 | | 2.32E−05 | |
| Probability % | 100.0 | | 100.0 | |
| % Difference | 50 | | 90.6 | |

TABLE 3A

|  | Days to Maturity |
|---|---|
| Sturgis | 71 |
| Prara | 69 |
| Frontier | 71 |

TABLE 3B

|  | Core Length (mm) | | Head wt. (g) | |
|---|---|---|---|---|
| Sample # | Sturgis | Prara Cos | Sturgis | Prara Cos |
| 1 | 49 | 62 | 798 | 705 |
| 2 | 50 | 60 | 800 | 689 |
| 3 | 53 | 67 | 816 | 654 |
| 4 | 50 | 62 | 798 | 780 |
| 5 | 54 | 65 | 796 | 743 |
| 6 | 50 | 59 | 700 | 802 |
| 7 | 50 | 65 | 812 | 675 |
| 8 | 54 | 68 | 856 | 621 |
| 9 | 53 | 59 | 784 | 678 |
| 10 | 48 | 65 | 845 | 600 |
| 11 | 45 | 59 | 712 | 703 |
| 12 | 50 | 59 | 878 | 684 |

TABLE 3B-continued

| | Core Length (mm) | | Head wt. (g) | |
|---|---|---|---|---|
| Sample # | Sturgis | Prara Cos | Sturgis | Prara Cos |
| Average | 50.5 | 62.5 | 799.6 | 694.5 |
| Stan dev | 2.65E+00 | 3.37E+00 | 5.19E+01 | 5.89E+01 |
| T test | 2.09E−09 | | 1.28E−04 | |
| Probability % | 100.0 | | 100.0 | |
| % Difference | 80.8 | | 86.9 | |

TABLE 3C

| | Core Length (mm) | | Plant Height (cm) | |
|---|---|---|---|---|
| Sample # | Sturgis | Frontier | Sturgis | Frontier |
| 1 | 49 | 100 | 26 | 30 |
| 2 | 50 | 85 | 29 | 31 |
| 3 | 53 | 115 | 30 | 30 |
| 4 | 50 | 100 | 30 | 30 |
| 5 | 54 | 120 | 27 | 33 |
| 6 | 50 | 85 | 25 | 33 |
| 7 | 50 | 90 | 28 | 30 |
| 8 | 54 | 110 | 29 | 31 |
| 9 | 53 | 100 | 28 | 30 |
| 10 | 48 | 105 | 28 | 34 |
| 11 | 45 | 94 | 27 | 31 |
| 12 | 50 | 100 | 29 | 30 |
| Average | 50.5 | 100.3 | 28.0 | 31.1 |
| Stan dev | 2.65E+00 | 1.10E+01 | 1.54E+00 | 1.44E+00 |
| T test | 3.57E−13 | | 4.50E−05 | |
| Probability % | 100 | | 100.0 | |
| % Difference | 50.3 | | 90.1 | |

TABLE 4A

| | Days to Maturity |
|---|---|
| Sturgis | 67 |
| Prara | 63 |
| Frontier | 66 |

TABLE 4B

| | Core Length (mm) | | Head wt. (g) | |
|---|---|---|---|---|
| Sample # | Sturgis | Prara Cos | Sturgis | Prara Cos |
| 1 | 65 | 82 | 750 | 582 |
| 2 | 67 | 84 | 748 | 598 |
| 3 | 50 | 79 | 790 | 656 |
| 4 | 56 | 80 | 834 | 534 |
| 5 | 79 | 74 | 784 | 569 |
| 6 | 65 | 75 | 700 | 590 |
| 7 | 65 | 72 | 759 | 678 |
| 8 | 68 | 89 | 658 | 500 |
| 9 | 56 | 73 | 790 | 525 |
| 10 | 58 | 74 | 769 | 555 |
| 11 | 60 | 79 | 800 | 600 |
| 12 | 60 | 70 | 756 | 598 |
| Average | 62.4 | 77.6 | 761.5 | 582.1 |
| Stan dev | 7.48E+00 | 5.58E+00 | 4.65E+01 | 5.11E+01 |
| T test | 1.16E−05 | | 8.02E−09 | |
| Probability % | 100.0 | | 100.0 | |
| % Difference | 80.5 | | 76.4 | |

TABLE 4C

| | Core Length (mm) | | Plant Height (cm) | |
|---|---|---|---|---|
| Sample # | Sturgis | Frontier | Sturgis | Frontier |
| 1 | 65 | 110 | 30 | 32 |
| 2 | 67 | 145 | 29 | 31 |
| 3 | 50 | 110 | 27 | 30 |
| 4 | 56 | 65 | 25 | 34 |
| 5 | 79 | 65 | 29 | 33 |
| 6 | 65 | 105 | 30 | 34 |
| 7 | 65 | 110 | 30 | 34 |
| 8 | 68 | 75 | 32 | 33 |
| 9 | 56 | 80 | 31 | 31 |
| 10 | 58 | 120 | 30 | 30 |
| 11 | 60 | 105 | 27 | 30 |
| 12 | 60 | 75 | 29 | 29 |
| Average | 62.4 | 97.1 | 29.1 | 31.8 |
| Stan dev | 7.48E+00 | 2.48E+01 | 1.93E+00 | 1.82E+00 |
| T test | 1.28E−04 | | 2.08E−03 | |
| Probability % | 100.0 | | 99.8 | |
| % Difference | 64.3 | | 91.6 | |

*Sturgis* most closely resembles its maternal parent variety Prara Cos, as both varieties are dark green romaine type lettuce. *Sturgis* is distinct from Prara Cos by the following characteristics:

*Sturgis* is slower growing, and matures later than Prara Cos

*Sturgis* has a higher resistance to tip burn than Prara Cos

*Sturgis* is slower bolting than Prara Cos

*Sturgis* forms a denser and heavier heart than Prara Cos

*Sturgis* is resistant to the Tombusvirus known as Tomato Bushy Stunt.

*Sturgis* is also distinct and unique from its paternal parent variety Frontier Cos.

*Sturgis* is darker in color than Frontier Cos

*Sturgis* is a smaller, more compact plant than Frontier Cos

*Sturgis* is resistant to the Tombusvirus known as Tomato Bushy Stunt.

*Sturgis* is distinct from the commercial variety Triple Threat based on the following characteristics.

*Sturgis* is darker in color than Triple Threat

*Sturgis* is slower bolting Triple Threat

*Sturgis* is a smaller more compact plant than Triple Threat

*Sturgis* has a denser and heavier heart than Triple Threat

The most distinguishing characteristic of this variety is its unique resistance to the Tombusvirus known as Tomato Bushy Stunt. A comparison of the mortality from Tomato Bushy Stunt between *Sturgis* and the varieties Frontier and Prara Cos is shown in Tables 5-8. The commercially available variety, Triple Threat, also appears to show some resistance to Tomato Bushy Stunt. *Sturgis* differs from Triple Threat. Triple Threat is lighter colored and has a smoother leaf surface than *Sturgis*. Furthermore, *Sturgis* has a smaller plant size than Triple Threat.

Results from Trial Evaluation of Mortality from Tomato Bushy Stunt Virus

TABLE 5

| | % Mortality from Tomato Bushy Stunt | |
|---|---|---|
| Replication | Sturgis | Frontier |
| 1 | 10 | 60 |
| 2 | 0 | 50 |
| 3 | 0 | 40 |
| 4 | 10 | 60 |

TABLE 5-continued

| Replication | % Mortality from Tomato Bushy Stunt | |
|---|---|---|
| | Sturgis | Frontier |
| 5 | 0 | 70 |
| 6 | 0 | 30 |
| 7 | 0 | 60 |
| 8 | 20 | 50 |
| 9 | 0 | 40 |
| 10 | 0 | 50 |
| Avg | 4 | 51 |
| std dev | 6.633249581 | 11.97219 |
| Ttest | 3.03177E−09 | |
| Probability | 100.00 | |

TABLE 6

| Replication | % Mortality from Tomato Bushy Stunt | |
|---|---|---|
| | Sturgis | Prara Cos |
| 1 | 10 | 50 |
| 2 | 0 | 70 |
| 3 | 0 | 60 |
| 4 | 10 | 50 |
| 5 | 0 | 70 |
| 6 | 0 | 80 |
| 7 | 0 | 90 |
| 8 | 20 | 60 |
| 9 | 0 | 70 |
| 10 | 0 | 80 |
| Avg | 4 | 68 |
| std dev | 6.633249581 | 18.56439045 |
| Ttest | 6.75326E−11 | |
| Probability | 100.00 | |

TABLE 7

| Replication | % Mortality from Tomato Bushy Stunt | |
|---|---|---|
| | Sturgis | Frontier |
| 1 | 0 | 80 |
| 2 | 0 | 85 |
| 3 | 0 | 90 |
| 4 | 0 | 86 |
| 5 | 0 | 85 |
| 6 | 0 | 70 |
| 7 | 0 | 55 |
| 8 | 0 | 100 |
| 9 | 0 | 90 |
| 10 | 0 | 80 |
| Avg | 0 | 82.1 |
| std dev | 0 | 12.32387024 |
| Ttest | 3.92064E−14 | |
| Probability | 100.00 | |

TABLE 8

| Replication | % Mortality from Tomato Bushy Stunt | |
|---|---|---|
| | Sturgis | Prara Cos |
| 1 | 0 | 80 |
| 2 | 0 | 80 |
| 3 | 0 | 80 |
| 4 | 0 | 90 |
| 5 | 0 | 90 |
| 6 | 0 | 80 |
| 7 | 0 | 50 |
| 8 | 0 | 60 |
| 9 | 0 | 80 |
| 10 | 0 | 90 |
| Avg | 0 | 78 |
| std dev | 0 | 13.16561177 |
| Ttest | 2.96649E−13 | |
| Probability | 100.00 | |

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

I claim:

1. A lettuce seed designated as *Sturgis* having ATCC Accession Number PTA-7228.

2. A lettuce plant produced by growing the seed of claim 1.

3. A plant part from the plant of claim 2.

4. The plant part of claim 3 wherein said part is a head.

5. The plant part of claim 3 wherein said part is a leaf or a portion thereof.

6. A lettuce plant having all the physiological and morphological characteristics of the lettuce plant of claim 2.

7. A plant part from the plant of claim 6.

8. The plant part of claim 7 wherein said part is a head.

9. The plant part of claim 7 wherein said part is a leaf or a portion thereof.

10. Pollen of the plant of claim 2.

11. An ovule of the plant of claim 2.

12. A tissue culture of the plant of claim 2.

13. A method of making lettuce seeds comprised of crossing the plant of claim 2 with another lettuce plant and harvesting seed therefrom.

14. A method of making an $F_1$ hybrid lettuce variety comprising:

crossing a lettuce plant with a plant grown from the *Sturgis* lettuce seed of claim 1; and selecting seed from said crossing.

* * * * *